(12) United States Patent
Tseytlin

(10) Patent No.: US 10,578,703 B2
(45) Date of Patent: Mar. 3, 2020

(54) FULL CYCLE RAPID SCAN EPR AND DECONVOLUTION

(71) Applicant: Colorado Seminary Watch Owns and Operates the University of Denver, Denver, CO (US)

(72) Inventor: Mark Tseytlin, Morgantown, WV (US)

(73) Assignee: Colorado Seminary Which Owns and Operates the University of Denver, Denver, CO (US)

( * ) Notice: Subject to any disclaimer, the term of this patent is extended or adjusted under 35 U.S.C. 154(b) by 32 days.

(21) Appl. No.: 15/941,936

(22) Filed: Mar. 30, 2018

(65) Prior Publication Data

US 2019/0302213 A1 Oct. 3, 2019

(51) Int. Cl.
- G01R 33/60 (2006.01)
- G06F 9/445 (2018.01)
- G01R 33/36 (2006.01)

(52) U.S. Cl.
CPC ......... *G01R 33/60* (2013.01); *G01R 33/3607* (2013.01); *G06F 9/445* (2013.01)

(58) Field of Classification Search
CPC ..... G01R 33/62; G01R 33/60; G01R 33/3607
See application file for complete search history.

(56) References Cited

U.S. PATENT DOCUMENTS

| | | | | |
|---|---|---|---|---|
| 2010/0148776 A1* | 6/2010 | Subramanian | ......... | G01R 33/60 324/310 |
| 2012/0262176 A1* | 10/2012 | Czechowski | .......... | G01N 24/10 324/316 |
| 2013/0119986 A1* | 5/2013 | Hirata | .................... | G01R 33/60 324/316 |

FOREIGN PATENT DOCUMENTS

WO 2014043513 A2 3/2014

OTHER PUBLICATIONS

Sweiger, et al., "Principles of Pulse Electron Paramagnetic Resonance", Jan. 1, 2001, p. 578 Publisher: Oxford University Press, Inc., Published in : US.

Biller, et al., "Imaging of Nitroxides at 250 MHZ Using Rapid-Scan Electron", "Journal of Magnetic Resonance", May 1, 2014, p. 19 vol. 242, Publisher: NIH, Published in: US.

Biller, et al., "Improved Sensitivity for Imaging Spin Trapped Hydroxyl Radical at 250 MHZ", "Chemphyschem.", Feb. 23, 2015, p. 10 vol. 16, No. 3, Publisher: downloaded from www.ncbi.nlm.nih.gov/pmc, Published in: US.

Biller, et al., "Rapid Scan Electron Paramagnetic Resonance Opens New Avenues for Imaging Physiologically Important Parameters in Vivo", "Journal of Visualized Experiments", Sep. 26, 2016, p. 9 vol. 115, Publisher: www.jove.com, Published in: US.

(Continued)

*Primary Examiner* — Gregory H Curran
(74) *Attorney, Agent, or Firm* — Neugeboren O'Dowd PC

(57) ABSTRACT

Full-cycle rapid scan (RS) electron paramagnetic resonance (EPR) can be performed without the instability of prior art methods and with a higher scan rate than traditional half-scan methods. In particular, a full scan is performed, but the constant RF driving B-field can be mathematically represented as two step functions, each corresponding to one half of a full scan cycle. This mathematical representation can be carried through the deconvolution such that two deconvolutions, one for the up cycle and one for the down cycle, can be performed. The solutions to these two deconvolutions can then be summed to give a single spectrum having a higher signal-to-noise ratio than half-cycle RS scans.

18 Claims, 6 Drawing Sheets

(56) References Cited

OTHER PUBLICATIONS

Czechowski, T., et al., "Two-Dimensional Spectral-Spatial EPR Imaging With the Rapid Scan and Modulated Magnetic Field Gradient", "Journal of Magnetic Resonance", Mar. 20, 2014, p. 7 vol. 243, Publisher: Elsevier, Published in: US.
Dadok, J. et al., "Correlation NMR Spectroscopy", "Journal of Magnetic Resonance", Nov. 9, 1973, p. 6 vol. 13, Publisher: Journal of Magnetic Resonance, Published in: US.
Eaton, S., et al, "Rapid-Scan Electron Paramagnetic Resonance", "Handbook of Multifrequency Electron Paramagnetic Resonance: Data and Techniques", May 18, 2014, p. 64 Publisher: John Wiley & Sons, Published in: US.
Elajaili, et al., "Electron Spin Relaxation Times and Rapid Scan EPR Imaging of PH-Sensitive Amino Substituted Trityl Radicals", "Magn Reson Chem.", Apr. 1, 2015, p. 13 vol. 53, No. 4, Publisher: downloaded from www.ncbi.nlm.nih.gov/pmc, Published in: US.
Gromov, Igor, "Improving Signal-To-Noise in EPR", "Oral Presentation at Asia-Pacific EPR/ESR Symposium 2016", Aug. 28, 2016, p. 1 Published in: RU.
Frank, J., et al., "Injectable Linc-Buo Loaded Microspheres as in Vivo EPR Oxygen Sensors After Co-Implantation With Tumor Cells", "Free Radical Biology and Medicine", Nov. 4, 2015, p. 9 vol. 89, Publisher: Elsevier, Published in: US.
Gupta, R., et al, "Rapid Scan Fourier Transform NMR Spectroscopy", Oct. 23, 1973, p. 16 vol. 13, Publisher: Journal of Magnetic Resonance, Published in: US.
Hirata, et al., "A Loop Resonator for Slice-Selective in Vivo EPR Imaging in Rats", "Journal of Magnetic Resonance", Jan. 1, 2008, p. 19 vol. 190, No. 1, Publisher: downloaded from www.ncbi.nlm.nih.gov/pmc, Published in: US.
Jarvis, et al., "Phase 1 Clinical Trial of Oxychip, an Implantable Absolute P02 Sensor for Tumor Oximetry", Oct. 1, 2016, p. 2 vol. 96, No. 2, Publisher: International Journal of Radiation Oncology, Published in: US.
Joshi, et al., "Rapid-Scan EPR With Triangular Scans and Fourier Deconvolution to Recover the Slow-Scan Spectrum", "Journal of Magnetic Resonance", Apr. 14, 2005, p. 8 vol. 175, Publisher: Elsevier, Published in: US.
Mitchell, et al., "Comparison of Continuous Wave, Spin Echo, and Rapid Scan EPR of Irradiated Fused Quartz", "Radiat Meas.", Sep. 1, 2011, p. 10 vol. 46, No. 9, Publisher: Downloaded from www.ncbi.nlm.nih.gov/pmc/, Published in: US.
Mitchell, D., et al, "Electron Spin Relaxation and Heterogeneity of the 1:1 Alpha, Gamma-Bisdiphenylene-Beta-Phenylallyl (BDPA)/ Benzene Complex", "The Journal of Physical Chemistry", May 16, 2011, p. 5 Publisher: American Chemical Society, Published in: US.
Mitchell, et al., "Use of Rapid-Scan EPR to Improve Detection Sensitivity for Spin-Trapped Radicals", Jun. 4, 2013, p. 5 vol. 105, Publisher Biophysical Journal, Published in: US.
Mitchell, D., et al., "X-Band Rapid-Scan EPR of Nitroxyl Radicals", "Journal of Magnetic Resonance", Nov. 20, 2011, p. 6 vol. 214, Publisher: Elsevier, Published in: US.
Mitchell, D., et al., "X-Band Rapid-Scan EPR of Samples With Long Electron Spin Relaxation Times: A Comparison of Continuous Wave, Pulse and Rapid-Scan EPR", "Molecular Physics: An International Journal at the Interface Between Chemistry and Physics", Apr. 5, 2013, p. 11 Publisher Taylor & Francis, Published in: UK.
Pandian, R., et al., "Novel Particulate Spin Probe for Targeted Determination of Oxygen in Cells and Tissues", "Free Radical Biology & Medicine", Jul. 24, 2003, p. 11 vol. 35, Publisher: Elsevier, Published in: US.
Quine, et al., "Quantitative Rapid Scan EPR Spectroscopy at 258MHZ", "J Magn Reson", Jul. 1, 2010, p. 10, vol. 205, No. 1, Publisher: downloaded from ww.ncbi.nlm.nih.gov/pmc/, Published in: US.
Quine, R., et al., "A Resonated Coil Driver for Rapid Scan EPR", Sep. 18, 2012, p. 16 vol. 41B, Publisher: Concepts in Magnetic Resonance Part B, Published in: US.
Tseitlin, et al, "Background Removal Procedure for Rapid Scan EPR", "J Magn Reson.", Jan. 1, 2010, p. 12, vol. 196, No. 1, Publisher: downloaded from www.ncbi.nlm.nih.gov/pmc, Published in: US.
Tseitlin, et al., "Combining Absorption and Dispersion Signals to Improve Signal-To-Noise for Rapid Scan EPR Imaging", "J Magn Reson", Apr. 1, 2010, p. 13 vol. 203, No. 2, Publisher: Downloaded from www.ncbi.nlm.nih.gov/pmc, Published in: US.
Tseitlin, et al., "Computationally Efficient Steady-State Solution of the Bloch Equations for Rapid Sinusoidal Scans Based on Fourier Expansion in Harmonics of the Scan Frequency", "Appl Magn Reson.", Dec. 1, 2013, p. 7 vol. 44, No. 12, Publisher: downloaded from www.ncbi.nlm.nih.gov/pmc, Published in: US.
Tseitlin, M., et al., "Corrections for Sinusoidal Background and Non-Orthogonality of Signal Channels in Sinusoidal Rapid Magnetic Field Scans", "J Magn Reson", Oct. 1, 2012, p. 13 vol. 223, Publisher: downloaded from www.ncbi.nlm.nih.gov/pmc, Published in: US.
Tseitlin, M., et al., "Deconvolution of Sinusoidal Rapid EPR Scans", "J Magn Reson", Feb. 1, 2011, p. 13 vol. 208, No. 2, Publisher: downloaded from www.ncbi.nlm.nih.gov/pmc, Published in: US.
Tseitlin, et al., "Digitally Generated Excitation and Near-Baseband Quadrature Detection of Rapid Scan EPR Signals", "J Magn Reson", Dec. 1, 2014, p. 21 vol. 249, Publisher: downloaded from www.ncbi.nlm.nih.gov/pmc, Published in: US.
Tseitlin, et al., "New Spectral-Spatial Imaging Algorithm for Full EPR Spectra of Multiline Nitroxides and PH Sensitive Trityl Radicals", "J Magn Reson", Aug. 1, 2014, p. 14 vol. 245, Publisher: www.ncbi.nlm.nih.gov/pmc/, Published in: US.
Yu, et al., "Rapid-Scan EPR of Immobilized Nitroxides", "J Magn Reson", Oct. 1, 2014, p. 15 vol. 247, Publisher: downloaded from www.ncbi.nlm.nih.gov/pmc/, Published in: US.

* cited by examiner

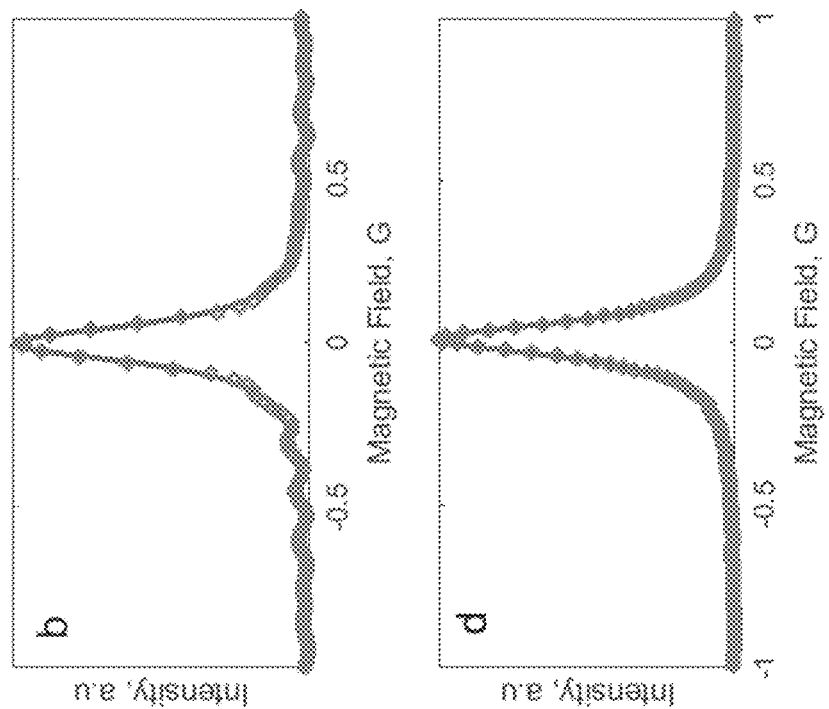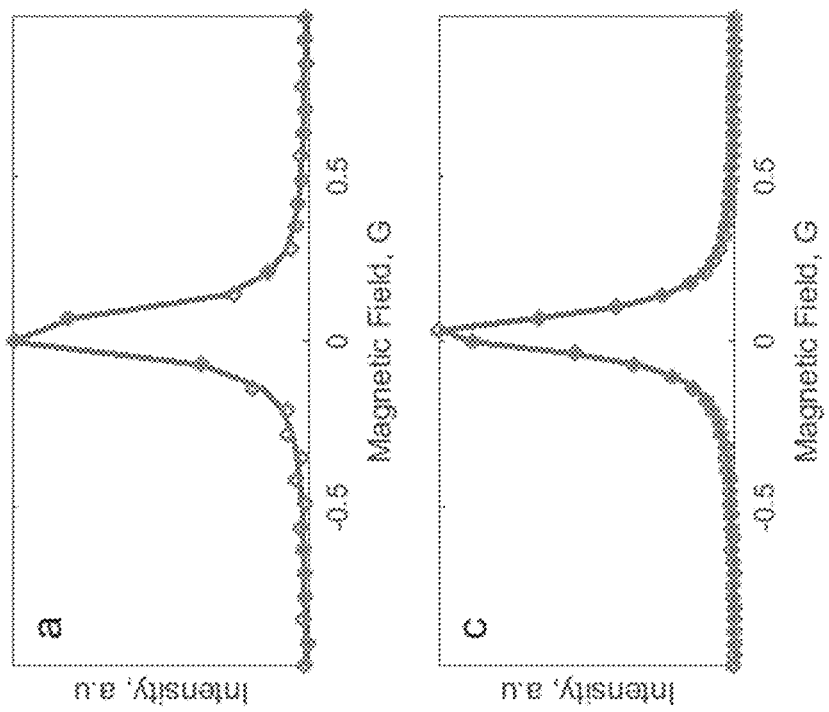
FIG. 4

FULL CYCLE RAPID SCAN EPR AND DECONVOLUTION

GOVERNMENT SUPPORT CLAUSE

This invention was made with Government support under Contract No. R21EB02277 awarded by the National Institutes of Health. The Government has certain rights in the invention.

FIELD OF THE DISCLOSURE

The present disclosure relates generally to electron paramagnetic resonance (EPR) scanning, and more particularly to methods and systems for deconvolving signals generated from EPR scanning.

BACKGROUND

In general, electron paramagnetic resonance (EPR) is used to study materials with unpaired electrons by exciting electron spins with magnetic fields and then measuring the field generated by the relaxation of the electrons. EPR can be conducted using continuous wave (CW) excitation (varying strength of an applied magnetic field) or pulsed excitation (pulsed microwave fields inducing a magnetic field) applied to the electrons. As any of these excitation sources is scanned, or varied, across a range, there comes an energy of excitation that causes the electron spins to flip and this magnetic absorption or resonance is seen as an absorption maximum in the EPR signal spectrum. By identifying excitation energies associated with the observed absorption maximum or maxima, one can identify characteristics of the material being studied.

Rapid Scan (RS) EPR is a recently developed CW method that combines narrowband excitation and broadband detection. In RS EPR, sinusoidal magnetic field scans that span the entire EPR spectrum cause electron spin excitations twice during the scan period. Periodic transient RS signals are digitized and time-averaged. Deconvolution of these RS signals is required in order to identify their relevant characteristics and distinguish the RS signals from background noise. Deconvolution of absorption spectrum from the measured full-cycle signal is an ill-posed problem (a unique solution may not exist or/and be unstable) that does not have a stable solution because the magnetic field passes the same EPR line twice per sinusoidal scan during up- and down-field passages. As a result, RS signals consist of two contributions that need to be separated and postprocessed individually. Deconvolution of either of the contributions is a well-posed problem that has a stable solution. Prior methods solve the separation problem by cutting the full-scan signal into two half-period pieces and then using an algorithm to deconvolve each separately. However, such prior methods impose undesired limitations on RS EPR experiments. Therefore, a need exists to improve upon the existing methods.

SUMMARY

An aspect of the present disclosure provides a method for full-cycle rapid scan (RS) electron paramagnetic resonance (EPR). The method can include performing a full-cycle RS EPR scan. This scan can pass through a resonance of target electrons twice per cycle. Yet, unlike convention scans, the scan frequency can be high enough that an RS response signal generated in response to the full-cycle RS EPR scan passing through a first of these two resonances does not decay by the time the full-cycle RS EPR scan passes through the second resonance. The method can further include transforming the RS response signal of the full-cycle RS EPR scan into a reference frame associated with a Larmor frequency of spins of the target electrons measured by the full-cycle RS EPR scan. The method can yet further include mathematically representing a constant RF driving magnetic field of the scan as a sum of two step functions offset by a half cycle. The method can yet further include performing two deconvolutions, with one of the two step functions (e.g., $B_1^{up}(t)$) as an input to a first of the two deconvolutions and a second of the two step functions (e.g., $B_1^{dn}(t)$) as an input to a second of the two deconvolutions, to form first and second deconvolution solutions. The method can yet further include summing the first and second deconvolution solutions to generate a spectrum with a higher signal-to-noise ratio than either of the deconvolution solutions alone.

Another aspect of the disclosure provides a system for full-cycle RS EPR. The system can include a processing portion with one or more processing components therein, a memory coupled to the processing portion, and a full-cycle RS EPR scanning module stored on the memory. The module can be executable on the processing portion to perform a full-cycle RS EPR scan. This scan can pass through a resonance of target electrons twice per cycle. Yet, unlike convention scans, the scan frequency can be high enough that an RS response signal generated in response to the full-cycle RS EPR scan passing through a first of these two resonances does not decay by the time the full-cycle RS EPR scan passes through the second resonance. The module can also be executable to transform the RS response signal of the full-cycle RS EPR scan into a reference frame associated with a Larmor frequency of spins of the target electrons measured by the full-cycle RS EPR scan. The module can also be executable to mathematically represent a constant RF driving magnetic field of the scan as a sum of two step functions offset by a half cycle. The module can further be executable to perform two deconvolutions, with one of the two step functions (e.g., $B_1^{up}(t)$) as an input to a first of the two deconvolutions and a second of the two step functions (e.g., $B_1^{dn}(t)$) as an input to a second of the two deconvolutions, to form first and second deconvolution solutions. The module can yet further be executable to sum the first and second deconvolution solutions to generate a spectrum with a higher signal-to-noise ratio than either of the deconvolution solutions alone.

Yet another aspect of the disclosure provides a non-transitory, computer-readable storage medium, encoded with processor readable instructions to perform a method for full-cycle RS EPR. The method can include performing a full-cycle RS EPR scan. This scan can pass through a resonance of target electrons twice per cycle. Yet, unlike convention scans, the scan frequency can be high enough that an RS response signal generated in response to the full-cycle RS EPR scan passing through a first of these two resonances does not decay by the time the full-cycle RS EPR scan passes through the second resonance. The method can further include transforming the RS response signal of the full-cycle RS EPR scan into a reference frame associated with a Larmor frequency of spins of the target electrons measured by the full-cycle RS EPR scan. The method can yet further include mathematically representing a constant RF driving magnetic field of the scan as a sum of two step functions offset by a half cycle. The method can yet further include performing two deconvolutions, with one of the two step functions (e.g., $B_1^{up}(t)$) as an input to a first of the two deconvolutions and a second of the two step functions (e.g., $B_1^{dn}(t)$) as an input to a second of the two deconvolutions, to form first and second deconvolution solutions. The method can yet further include summing the first and second deconvolution solutions to generate a spectrum with a higher signal-to-noise ratio than either of the deconvolution solutions alone.

BRIEF DESCRIPTION OF THE DRAWINGS

FIG. 4 shows a series of EPR spectra in the magnetic field domain;

DETAILED DESCRIPTION

Figure 1:
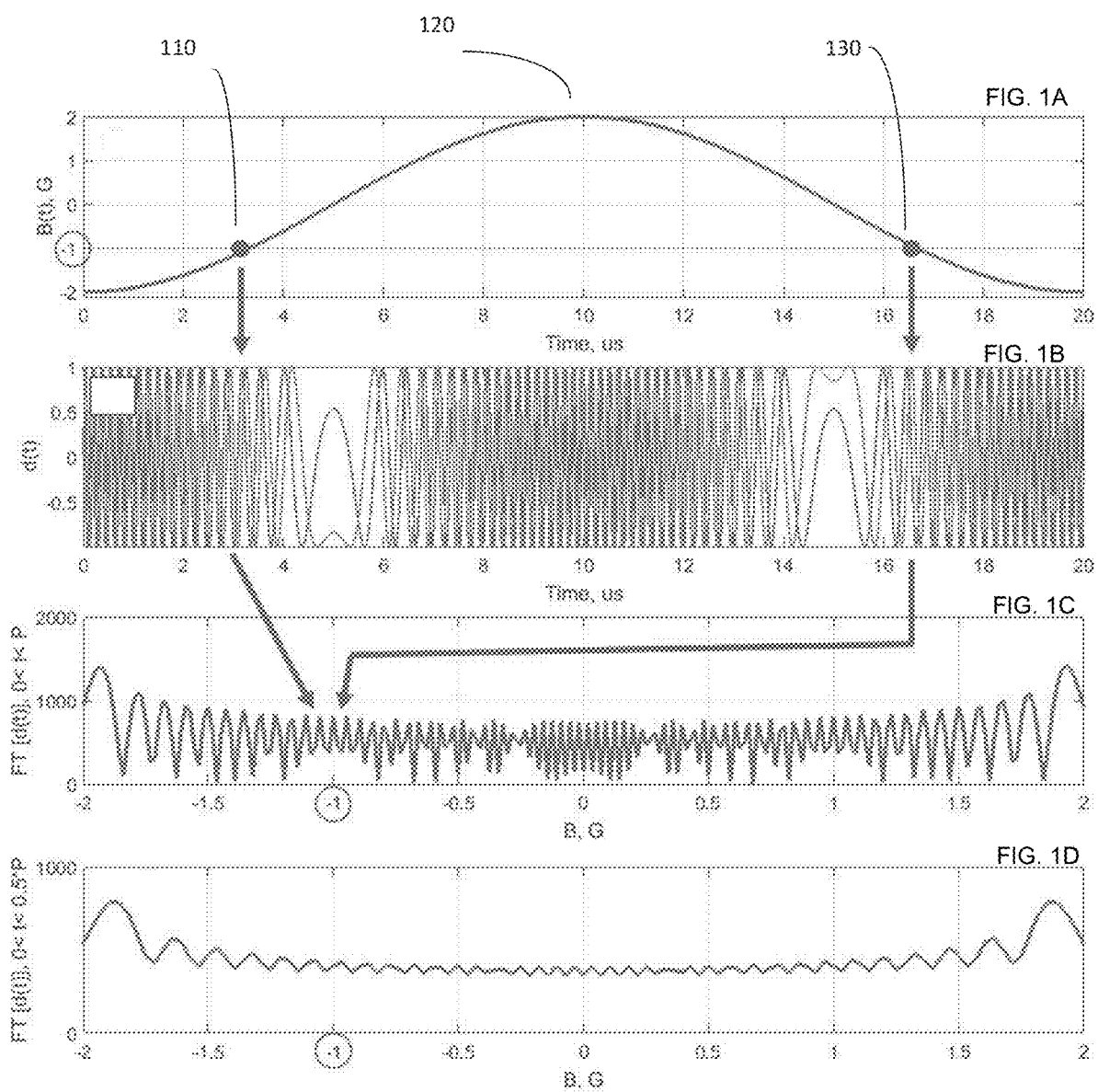
FIG. 1A shows an exemplary sinusoidal scan of the magnetic field as a function of time where the field crosses resonance once on the up scan and once on the down scan.
FIG. 1B shows a plotting of a driving function, d(t), as a function of time.
FIG. 1C shows a Fourier Transformed plot of FIG. 1B in the magnetic field domain as deconvolved over a full cycle, 0<t<P.
FIG. 1D shows a Fourier Transformed plot of FIG. 1B in the magnetic field domain as deconvolved over a half cycle, 0<t<P/2.

Conventional continuous-wave (CW) spectrometers, which operate on principles developed in the last century, remain the predominant kinds of electron paramagnetic resonance (EPR) instruments used worldwide. EPR is a method commonly used for the detection of paramagnetic species, and has applications in many fields of biology and quantum physics. Magnetic field modulation with an amplitude smaller than the spectral linewidth is used to measure first-derivative spectra. The standard CW experiment known in the art is not optimized for EPR sensitivity but rather for simplicity of data acquisition and processing, which was an important requirement in the pre-digital era. Commercially available fast digitizers and computers have made it possible to reinvent the CW method. For example, instead of exciting only a small fraction of electron spins, the amplitude of the sinusoidal modulation can be increased by one to two orders of magnitude to encompass the entire EPR spectrum. All paramagnetic centers in the sample would contribute to the EPR signal twice during the modulation period, resulting in a signal gain. Because the spin system is not readily saturated in the rapid passage regime, a higher excitation power than in the standard experiment can be used without causing spectral distortions. Improved sensitivity comes with a data processing challenge. Fast magnetic field scans generate transient signals, analogous to free induction decay (FID) responses to an excitation pulse.

The mathematical problem of signal-spectrum transformation was solved in the last century for nuclear magnetic resonance and recently for EPR for the special case of a linear scan. The development of an algorithm that permits the use of a sinusoidal magnetic field stimulus was a turning point in the evolution of CW EPR because producing a single harmonic current is much less of an engineering challenge compared to generation of a saw-tooth waveform in a coil. The coil inductance can be compensated with a capacitor to make a resonance circuit for a specific frequency. Fast scans that span over wide EPR spectra can be produced.

The rapid scan (RS) EPR method of generating and processing transient responses to the sinusoidal magnetic field stimulus is documented in co-owned and co-pending patent application Ser. No. 14/419,907. The version of the RS EPR algorithm discussed in application Ser. No. 14/419,907 solves an ill-posed problem—that the solution is unstable to small variations in the experimental parameters and noise—as two independent well-posed problems. Full-cycle RS signals are divided into two halves for up- and down-field scans, and each component is deconvolved separately. For the purposes of the present disclosure, the version of the algorithm described in application Ser. No. 14/419,907 will be referred to herein as the "half-scan RS EPR algorithm" or, alternatively, "half-scan deconvolution algorithm." A half-cycle RS EPR algorithm is another way to characterize the previous method since two half-cycle scans are performed and deconvolved separately.

The half-scan RS EPR algorithm imposes a restriction on scans themselves: transverse magnetization must decay completely by the end of each half-scan to avoid truncation of the signals. This limits the scan frequency and, therefore, the sensitivity. The present disclosure describes a full scan deconvolution algorithm that does not require signal truncation because it utilizes the additive property of linear time-invariant systems. The method of the present disclosure will be referred to throughout as the "full-scan deconvolution algorithm" or, alternatively, "full-cycle algorithm." The full-cycle algorithm involves a decoupling of up- and down-field scan contributions to the RS signal. The use of previously developed background removal procedure permits frequency domain separation of the contributions. However, the method does not work if the up- and down-scan signals overlap. As a result, only a two-fold increase in the scan rate can be achieved, in comparison with the previous half-scan RS EPR deconvolution algorithm. It is contemplated that further development of new signal separation methods may enable the algorithm of the present disclosure to work on overlapping up-and-down scan signals and permit the use of frequencies above a two-fold increase.

The experiments and equations described in these paragraphs provide the background theory upon which the method of the present disclosure was developed. An experimentally measured RS signal is an averaged, amplified, and down-converted response of the spin system m(t):

$$m(t)=m_x(t)+jm_y(t) \quad \text{Equation 1:}$$

to a stimulus in the form of a sinusoidal magnetic field:

$$B(t)=-0.5B_{pp}\cos(2\pi f_s t) \quad \text{Equation 2:}$$

in the presence of CW excitation. $B_{pp}$ is the peak-to-peak amplitude, and $f_s$ is the frequency of the alternating field. Because periodic stimulation, B(t), produces periodic response:

$$m(t)=m(t+P), P=1/f_s \quad \text{Equation 3:}$$

measurement of transient EPR coherences that last longer than P can be problematic.

Linear System Approximation

The herein disclosed full-scan rapid scan data processing algorithm assumes that the spin system is well-approximated as a linear time-invariant system (LTI). Any LTI system is uniquely characterized by the impulse response function, which is an FID in the case of magnetic resonance. The FID is an outcome of an excitation in the form of an infinitely narrow pulse. Within the LTI assumption, an arbitrary pulse, $B_1(t)$, produces response m(t):

$$m(t)=B_1(t)\otimes \text{FID}(t), \quad \text{Equation 4:}$$

where $\otimes$ represents the convolution operator in Equation 4. If an input $B^a_1(t)$ produces an output $m^a(t)$ and an input $B^b_1(t)$ generates an output $m^b(t)$, then the sum of the inputs give the sum of the outputs:

$$(B_1^a+B_1^b)\otimes \text{FID}=B_1^a\otimes \text{FID}+B_1^b\otimes \text{FID}=m^a+m^b=m \quad \text{Equation 5:}$$

Dependence on time in the above equation is omitted for better readability. An important point of the full scan deconvolution algorithm described below is that equation 5 above can also be used in reverse. An actual excitation field, $B_1(t)$, can be represented as a sum of two arbitrary functions, and the spin response observed in the experiment can also be separated into two contributions corresponding to each of the inputs. Using the well-known property of Fourier transformation (FT), convolution in Equation 4 described above can be changed into multiplication in the frequency domain:

$$\text{FT}[m(T)]=\text{FT}[B_1(t)]\text{FT}[\text{FID}(t)] \quad \text{Equation 6:}$$

EPR spectrum $S(\omega)$ can be found from Equation 6, as follows:

$$S(\omega)=\text{FT}[\text{FID}(t)]=\text{FT}[m(t)]/\text{FT}[B_1(t)] \quad \text{Equation 7:}$$

Because both $B_1(t)$ and m(t) functions are periodic, FID(t) is also periodic with the same period P. As a result, any spin response signal that lasts longer than P cannot be measured without truncation:

$$1/f_s > P_{min} = 5T_2^* \quad \text{Equation 8:}$$

Equation 8, in which $T_2^*$ is an observed transverse relaxation time, establishes the upper theoretical limit for the scan frequency $f_s$.

The spin system is well-approximated as LTI in the conventional CW experiment if the excitation power is below the saturation level. In contrast, in the herein disclosed rapid scan regime, Equations 4-7 are valid at higher powers. In the extreme case of the scan frequency approaching the limit given by Equation 8, the rapid scan signal resembles that of an FID in the pulsed EPR experiment. The spins experience a short-duration excitation as B(t) passes through the resonance. Free evolution of the spins in the changing B(t) field is observed after the excitation. In the system of coordinates associated with B(t)-driven Larmor frequency, the spins experience a short frequency modulated pulse (i.e., a chirp pulse).

Transformation into Reference Frame Associated with the Larmor Frequency

The conventional and herein disclosed Rapid Scan EPR is a CW experiment, meaning that the excitation field is time-independent in the frame associated with the excitation source frequency. Direct substitution of a constant B1 value in Eqs. (4-7) does not produce any meaningful results. In addition, there is also no explicit formulation of the scanning field B(t) within the LTI mathematical model. An aspect of the present disclosure is that this problem is overcome via transformation of the rapid scan signal into a reference frame associated with the Larmor frequency of the spins $\omega_L(t)$:

$$\omega_L(t)=\gamma B(t)=-0.5\gamma B_{pp}\cos(2\pi f_s t) \quad \text{Equation 9:}$$

To obtain a mathematical expression for the transformation, the phase difference between the laboratory and accelerating frames can be found. The phase gain starting from the beginning of the scan (t=0) can be found by integration of Equation 9 to give:

$$\varphi(t)=\int_0^t \gamma B(\tau)d\tau = -\frac{i\gamma B_{pp}}{4\pi f_s}\sin(2\pi f_s t). \quad \text{Equation 10}$$

In the frame associated with $\varphi(t)$, B(t)=0. The transformation into the system of coordinates associated with $\omega_L(t)$ can be achieved by multiplication:

$$\mu(t)=m(t)d(t), d(t)=\exp[-i\varphi(t)] \quad \text{Equation 11:}$$

For an observer in the new system of coordinates, the laboratory frame is accelerating, and the $B_1$ field becomes time-dependent:

$$B_1(t)'=B_1 d(t). \quad \text{Equation 12:}$$

Applying Equations 11-12 is equivalent to a change of the experiment; field-swept CW is replaced by frequency-swept EPR at a constant external field. The transformation permits Equation 4 to be rewritten in the form:

$$\mu(t)=B_1 d(t)*\text{FID}(t) \quad \text{Equation 13:}$$

As a result, deconvolution of EPR spectrum from rapid scan signals can be done as follows:

$$S(-B)=S(\omega/\gamma)\propto \text{FT}[\mu(t)]/\text{FT}[d(t)] \quad \text{Equation 14:}$$

The minus sign in front of B in Equation 14 reflects the fact that field and frequency scans occur in opposite directions. In the up-field scan CW experiment, the spins at a higher local field are observed first. An up-frequency scan at the constant external field excites these spins last.

Half-Cycle Deconvolution

Equation 14 is a classic example of deconvolution, which is often an ill-posed problem, meaning that a unique solution may not exist or/and be unstable, which is the case for rapid scan EPR. The absolute value of the denominator in Equation 14 is an oscillating function with multiple values approaching zero, as shown in FIG. 1C. Turning now to FIGS. 1A-D, the Figures provide a graphical explanation of how deconvolution of a full scan EPR is an ill-posed problem. FIG. 1A shows that a magnetic field passes through a resonance position (shown at point 110 in FIG. 1A) twice during the scan period (e.g., ~3 μs and 16.5 μs). FIG. 1B shows that function d(t) oscillates with the Larmor frequency $-\gamma$ (ca. $-2.8$ MHz) at these two times (i.e., when the magnetic field strength passes through the resonance position, or $B(t)=-1$ Gauss).

FIGS. 1C and 1D both show Fourier Transforms of the signal d(t) in FIG. 1B. However, FIG. 1C takes a Fourier Transform of the full scan period (e.g., 0<t<P, or about 20 μs in FIG. 1A) while FIG. 1D takes a Fourier Transform of half the scan period (e.g., 0<t<0.5P, or about 10 μs). The Fourier Transform of the full scan period sums two complex contributions corresponding to the same frequency to produce an interference pattern, while the Fourier Transform of the half scan period does not. Depending on the scan frequency and amplitude, the interference of the Fourier Transform of the full scan can be either constructive or destructive. As a result, when FT[d(t)] (i.e., the Fourier transform of d(t)) is in the denominator of Equation 14, there is instability in that deconvolution equation (the problem is ill-posed). In contrast, a half-scan of d(t) shown in FIG. 1D results in no interference at the resonance position $-1$ G. Consequently, the solution of Equation 14 is well-posed for a half-scan.

Thus, FIG. 1C shows that the value of the denominator in Equation 14 is an oscillating function with multiple values approaching zero, which is considered an unstable solution. This instability results because B(t) in FIG. 1A passes through the same value of the magnetic field twice during the period (B(t)=−1 G, as an example). The frequency with which d(t) oscillates (as shown in FIG. 1B) is equal to $\omega_L(t)$. After the Fourier transform, two contributions, corresponding to the same frequency but different time instances, are summed. If the contributions are in-phase with each other, there is a constructive interference. If they are 180° out-of-phase, they cancel each other and FT[d(t)] approaches zero. For some of the magnetic field strengths B(t) in the scan, the two contributions are constructive and others are destructive, as seen by the fact that FIG. 1C shows both higher and lower values across the scan than does FIG. 1D. The destructive interference means that the deconvolution problem in Equation 14 is ill-posed, and for two reasons. First, multiple near-zero values of the denominator in Equation 14 amplify noise. More importantly, the positions of the zeros strongly depend on the parameters of the scan. Miniscule uncertainty in the estimation of either the experimental scan amplitude and/or phase results is instability of the solution.

Thus, FIGS. 1C and 1D show why previous attempts have focused on half-scan approaches to arrive at a stable deconvolution, but at the sacrifice of scan speed. To enable faster scans, a full scan is desired, but without the instability seen in FIG. 1C.

Figure 2:
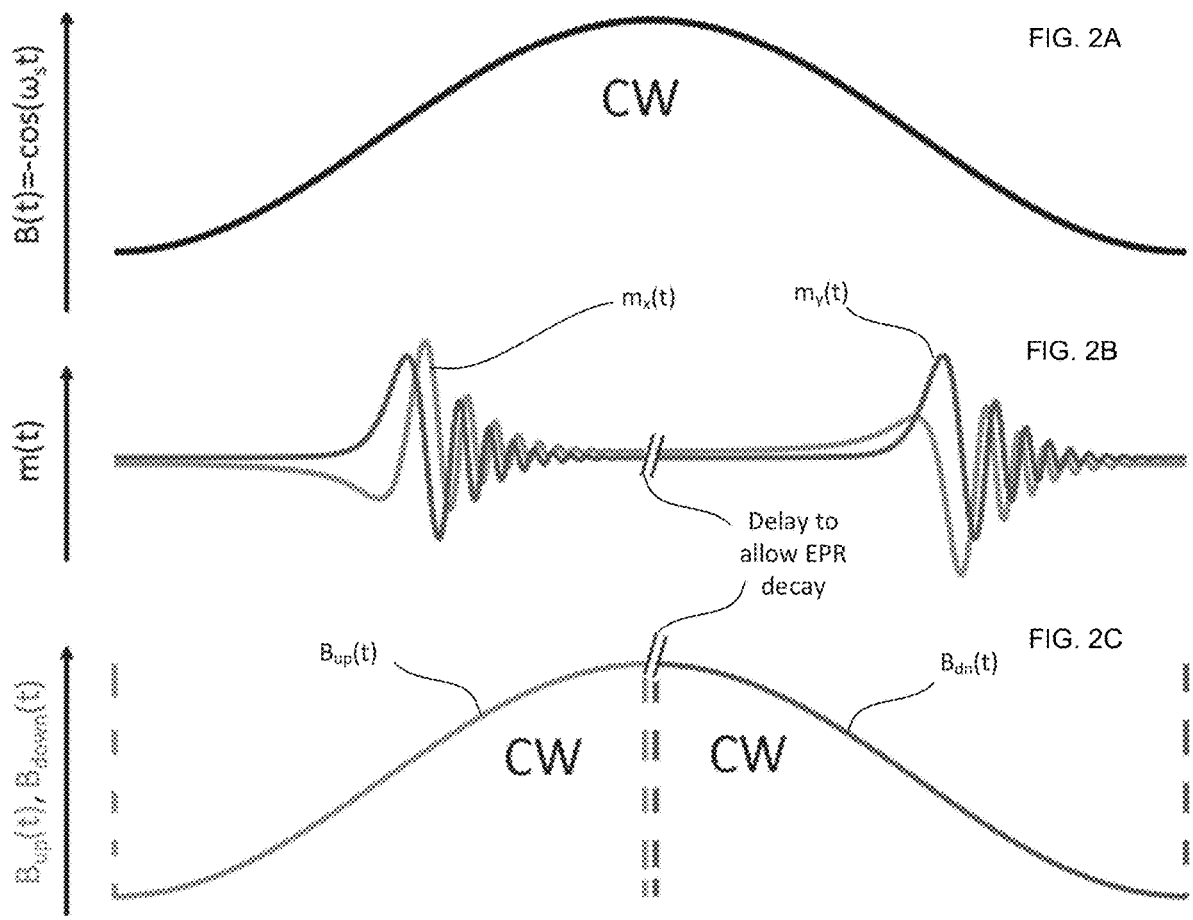
FIG. 2A shows another exemplary sinusoidal scan of the magnetic field as a function of time without truncation of the time scale.
FIG. 2B shows an EPR signal response, m(t), generated by a sinusoidal scan of the magnetic field, B(t) seen in FIG. 2C, where the time scale is truncated.
FIG. 2C shows a sinusoidal scan of the magnetic field as a function of time with a pause between an end of the up cycle and a start of the down cycle, where the time scale is truncated, to enable the resonant response to the up half of the cycle seen in FIG. 2B to decay.

FIGS. 2A-2C illustrate how a stable solution of the deconvolution problem for a full scan can be found. Specifically, this disclosure imposes a restriction on the rapid scan EPR process; transverse magnetization is allowed to completely decay by the end of the up- or down-scan. In this case, the full cycle rapid scan EPR signal can be separated into two halves (see FIG. 2B, described below), and each half-period piece can be deconvolved independently (see Equation 14) thereby avoiding destructive interference that otherwise leads to an unstable deconvolution. The half-period deconvolution can be performed as follows:

$$S^{up}(-B) \propto FT[\mu(t)]/FT[d(t)], 0 \leq t < P/2 \quad \text{Equation 15 (a)}$$

$$S^{dn}(-B) \propto FT[\mu(t+P/2)]/FT[d(t+P/2)], 0 \leq t < P/2 \quad \text{Equation 15 (b)}$$

Because B(t) doesn't pass through the same field twice, the denominators do not oscillate as much (i.e., more like FIG. 1D than FIG. 1D). As a result, the deconvolution problem becomes well-posed.

FIG. 2A shows a graph of a full-cycle scan, and FIG. 2C shows a graph of two half scans (one the first half for the up-cycle and the second half for the down-cycle). Changing the scan model from a full-cycle to a half cycle helps to find stable solutions for the deconvolution problem. FIG. 2B illustrates that if the RF signal completely decays before it reaches the inflection points of B(t), the up- and down-scan contributions can be separated. The $B_{up}(t)$ and $B_{down}(t)$ scans shown in FIG. 2C are periodic, as is B(t) itself. The period is equal to P/2. In both scan models shown in FIGS. 2A and 2C. In both models, the excitation field $B_1$ is CW.

However, to achieve faster scan rates, the restriction that the response m(t) decays by the inflection point of B(t) (or by the next resonance crossing) should be lifted. In other words, faster scan rates entail electron relaxation that carries past a half cycle. Said another way, there is no need to wait until an EPR signal has decayed to start the next half cycle. Said yet another way, the two EPR signals seen in FIG. 3A can overlap during measurement, but can be mathematically separated during processing. FIGS. 3A-3D demonstrate aspects of a novel measurement and deconvolution method according to this less restrictive method. This embodiment of full cycle deconvolution is based on the property of linear systems described in Equation 5. This embodiment does not require the limit on the decay period shown in FIG. 2B. Instead, the scan frequency can be fast enough such that EPR signals from the up and down portions of a scan (i.e., the two damped response signals seen in FIG. 3A) can overlap. For instance, in FIG. 3A the first EPR signal (e.g., from an up half of a cycle) continues to oscillate past where the next EPR signal (e.g., from a down half of the cycle) starts, and thus the up signal overlaps with a portion of the down signal. The prior art suggests that scan rates fast enough to cause this overlap in EPR signals from the up and down halves of a cycle causes problems. However, the instant disclosure enables such fast scan rates through a novel mathematical approach to separating these two overlapping signals.

There are three magnetic fields influencing measured electrons at the same time: a constant B-field, an RF field (having a constant frequency and sinusoidal shape), and the scanned or slow B-field (having a variable strength and constant sinusoidal frequency). This invention enables a faster scanned or slow B-field. This is made possible by the inventor's recognition that the constant RF field ($B_1$) could be represented as two step functions $B_1^{up}(t)$ and $B_1^{dn}(t)$ (e.g., see Equation 16 below and FIG. 3B; up-scan function 312 and down-scan function 314). Although not shown, the up and down halves of a cycle of the scanned or slow B-field align with $B_1^{up}(t)$ and $B_1^{dn}(t)$ in FIG. 3B.

$$B_1 = B_1^{up}(t) + B_1^{dn}(t), \quad \text{Equation 16}$$

$$B_1^{up}(t) = B_1 \, \theta(t) \, \theta(-t + P/2),$$

$$B_1^{dn}(t) = B_1 \, \theta(t - P/2) \, \theta(-t + P),$$

$$\theta(t) = \begin{cases} 1, t > 0 \\ 0, t < 0 \end{cases},$$

Figure 3:
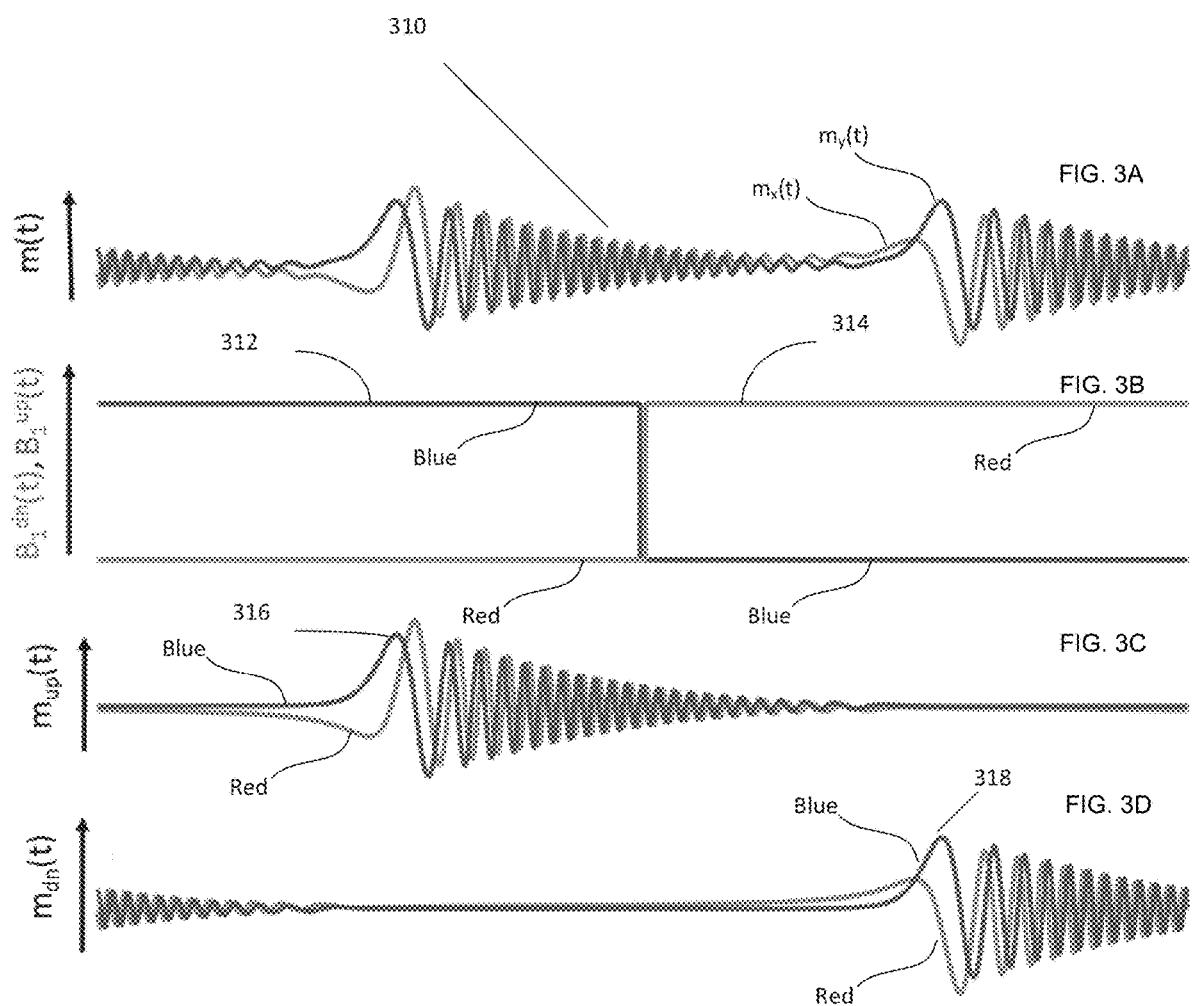
FIG. 3A shows an EPR response signal to a sinusoidally scanned magnetic field, where the scan frequency is high enough that a first EPR response signal does not decay entirely by a start of a second EPR response signal.
FIG. 3B shows a mathematical representation of the constant RF magnetic field, $B_1$, as a periodic series of step functions.
FIG. 3C shows the first EPR response signal separated from the combined signal of FIG. 3A.
FIG. 3D shows the second EPR response signal separated from the combined signal of FIG. 3A.

These two step functions are illustrated in FIG. 3B, which will be described presently. It should be understood that the actual applied RF field $B_1$ does not actually have a step function nor does it have up and down portions—equation 16 and FIG. 3B are merely mathematical complications of an otherwise simple concept—that the RF field is constant. While adding complexity to a system is counterintuitive, and thus non-obvious, the result is that this provides a mathematical way to deconvolve the EPR signal from the up and down halves of the cycle even where those signals overlap (i.e., even where the up EPR signal does not decay by the time the down EPR signal begins).

FIG. 3A shows a full-scan solution of Equation 14 that does not limit scan rates. FIGS. 3C and 3D, respectively, show the rapid scan signal m(t) (FIG. 3A) separated into its two corresponding excitation responses 316 (up) and 318 (down). This separation of the rapid scan signal m(t) allows deconvolution of each EPR signal separately, which permits a stable deconvolution of a whole scan as described by Equation 17 below. The exact and stable solution of the full scan deconvolution problem without scan rate restrictions can be found by using Equations 5, 13, and 14:

$$S^{up}(-B) \propto FT[\mu^{up}(t)] / FT[d(t)B_1^{up}(t)], 0 \leq t < P \quad \text{Equation 17(a)}$$

$$S^{dn}(-B) \propto FT[\mu^{dn}(t)] / FT[d(t)B_1^{dn}(t)], 0 \leq t < P \quad \text{Equation 17(b)}$$

Deconvolving Equations 17(a) and (b) and summing the results leads to a single spectrum solution with higher signal-to-noise than a half-cycle scan would, yet without the instability of other full-scan methods. It should be noted that the deconvolutions of Equation 17(a) and 17(b) provide the same spectrum result, but with different noise characteristics. Thus, adding these two solutions leads to a doubling of the signal components, while somewhat cancelling the noise components of both solutions and thus a higher signal-to-noise result. Equations 17(a) and 17(b) can be exact and stable because the denominators are well-defined functions. The challenge for the practical use of Equation 17 is to separate the rapid scan signal m(t) into two components, corresponding to $B_1^{up}(t)$ and $B_1^{dn}(t)$. The method that was developed for background removal in the half-cycle deconvolution algorithm can be used to accomplish this goal, which is described in co-pending and co-owned application Ser. No. 14/419,907.

Although the scan rate is greatly improved over the prior art, it can be somewhat limited by the bandwidth of the detection resonator, which acts as a band-pass filter for RS signals. In the example of FIG. 1, the transverse magnetization generated at the resonance position B(t)=−1 G (at point 110) will precess with increasing frequency until it reaches the highest point on the scan, B(t)=2 G (at point 120). At this point, the Larmor frequency will be approximately 9 MHz higher than the excitation frequency. The resonator bandwidth is preferably large enough to permit an undistorted detection of a 9 MHz component of the signal. As explained above, after passing the maximum field point on the scan, the precession frequency decreases, and the signal bandwidth remains the same. Thus, increasing the scan frequency for full-cycle deconvolution may be performed without reduction of the resonator quality factor, which may be detrimental to EPR sensitivity.

Another aspect of the disclosure relates to a sampling interval in the spectral dimension. Any periodic function has a discrete spectrum defined at the integer multipliers of the fundamental frequency. For this reason, FT of m(t) and d(t) are sampled with the interval equal to $d\omega = 2\pi f_s$ in the frequency domain. In the magnetic field domain, EPR spectra are discrete, with the sampling increment equal to:

$$\Delta B = 2\pi f_s / \gamma \quad \text{Equation 18:}$$

The number of points in the deconvolved spectrum is equal to $$Np = B_{pp} / \Delta B \quad \text{Equation 19:}$$

Np is rounded to the closest integer number. Because m(t) and d(t) functions are truncated in the half-scan algorithm, the effective scan frequency is twice as large so that the sampling interval is equal to $2\Delta B$ and the number of data points reduces to Np/2. Thus, EPR spectra become undersampled by a factor of two. This is not a problem if $f_s$ is relatively small but may be detrimental for high frequency scans that approach the limit of Equation 8.

The following paragraphs describe an experiment conducted to compare the half-cycle and full-cycle deconvolution methods at increasing scan frequency rates. The experimental method described herein is described for exemplary purposes only, and shows just one possible implementation of the full-cycle rapid scan and deconvolution method of the present disclosure.

Sample: Locally synthesized Lithium octa-n-butoxy 2,3-naphthalocyanine (LiNc-BuO) microcrystals were used to compare the half-cycle and full-cycle deconvolution algorithms. LiNC-BuO crystals were placed into a 1 mm ID tube, degassed, and flame-sealed. The sample height was approximately 2 mm. LiNC-BuO is used in EPR oximetry, including clinical applications as an oxygen sensitive core of the OxyChip, which is an implantable absolute pO(2) sensor used for tumor oximetry An RS EPR spectrometer/imager was used for the experiments. Though the experiments utilized the following components described, other suitable components may be used in various embodiments of spectrometers capable of implementing the full-cycle rapid scanning and deconvolution of the present disclosure. A permanent magnet (Ningbo Jansen NMR Technology Co) was equipped with sweep coils to produce a magnetic field in the range 268+/−25 G, which corresponds to a frequency span from 680 to 820 MHz. A single loop reflection resonator was manufactured using a previously described design for 300 MHz EPR imaging of rats. The sample was placed into a tube filled with salted water. The loaded quality factor, Q, was approximately 100 at a 767 MHz operating frequency. Rapid scan coils were locally built using Litz wire wound on a 3D printed plastic support structure that also accommodated a mouse bed, which was not used in the experiments described here.

Sinusoidal scans were produced by a Keysight 33622A arbitrary waveform generator (AWG). The AWG output was amplified using an 1800 watt Cerwin-Vega CV-1800 audio amplifier. The RS coils were resonated using a series of capacitors. The phase and amplitude of the current in the coils was measured using a Teledyne AP031 differential probe that was connected to the two terminals of a 100 nF capacitor. The probe output was measured with an NI PCIe 6363 DAQ card. The RF bridge, which was designed and built locally, output a baseband RS signal that was digitized using a Keysight U1084A high-speed digitizer. The card and external field were controlled by SpecMan4EPR software. The digitizer was phase-locked to the AWG using a 10 MHz external reference. RS signals were post-processed into absorption EPR spectra using locally-written Matlab software programs.

Comparison of Half-Cycle and Full-Cycle Deconvolution Methods:

RS data were collected at three scan frequencies: 29, 72, and 98 kHz. The signals were processed using the published half-cycle RS EPR algorithm and the new full-cycle deconvolution method. EPR spectra were fitted with a Lorentzian line-shape function using the Matlab Curve Fitting Tool (CFT). The CFT output the fitting results together with the confidence bounds at a level of 95% and root mean square errors (RMSE) of the fitting. The results are summarized in Table 1.

TABLE 1

Comparison of EPR line fitting results for half-cycle and full-cycle RS deconvolution algorithms. EPR spectra obtained at 98 kHz were interpolated.

| Scan frequency | Half-cycle algorithm | | Full-cycle algorithm | |
|---|---|---|---|---|
| | FWHM [mG] | RMSE *1e4 | FWHM [mG] | RMSE*1e4 |
| 29 kHz | 123 ± 2 | 62 | 123 ± 1 | 46 |
| 72 kHz | 131 ± 5 | 133 | 127 ± 1 | 51 |
| 98 kHz | 134 ± 9 | 182 | 130 ± 2 | 74 |
| 98 kHz (interpolated) | 135 ± 4 | 160 | 129 ± 1 | 65 |

At the lowest frequency of 29 kHz, the scan rate is relatively slow, and RS signals decay completely by the end of each half-scan. Both algorithms give similar half-magnitude (FWHM) linewidth estimations of 123 mG within narrow confidence intervals and low root square mean error (RSME). At higher scan frequencies, both algorithms show increases in FWHM. The fitting results of the spectra deconvolved using the half-cycle method demonstrate larger linewidth broadening, increased confidence intervals, and RSME. The uncertainty caused by under-sampling (see Equations 18, 19) can be partially reduced by interpolation using the Matlab routine interpft.

FIG. 4 demonstrates EPR spectra obtained using the two algorithms before (FIGS. 4A, 4C) and after (FIG. 4B, 4D) interpolation. FIG. 4A shows discrete points of EPR spectra obtained during a half-cycle RS deconvolution method, and FIG. 4C shows discrete points obtained using a full-cycle deconvolution method. As shown, the sampling rate for EPR spectra in FIG. 4C is twice as large as the sampling rate in FIG. 4A. A Fourier interpolation of the points shown in FIGS. 4A and 4C gives the points shown in FIGS. 4B and 4D, respectively. The solid lines in each of the FIGS. 4A-4D as the fitting functions of Lorentzian shape. FIGS. 4A and 4B demonstrate oscillations that are the result of RS signal truncation.

The experiment described in the previous paragraphs shows how the full-cycle deconvolution method may be successfully used to increase scan frequency without increasing signal bandwidth. The following paragraphs summarize the development of the full-cycle deconvolution method in view of the previously used half-cycle method and the results of the experiment showing the feasibility of implementing the full-cycle deconvolution method.

A sinusoidal magnetic field scan, B(t), passes through the same EPR line twice during the scan period. Periodic rapid scan signal is a response to two consequent spin system excitations. Recovery of the EPR spectrum from a transient signal is an ill-posed problem. However, in linear system approximations, periodic m(t) (FIG. 3A) can be represented as a sum of the responses (FIGS. 3C and 3D) to two excitations (FIG. 3B) that occur during up- and down-field scans. Based on this assumption, a half-scan deconvolution algorithm was developed that requires complete decay of the transverse magnetization by the end of each half-scan (see FIG. 2). The rapid scan signal m(t) is split into two equal pieces for 0<t<P/2 and P/2<t<P that are post-processed individually. The half-scan algorithm imposes an upper limit of the scan frequency and may generate under-sampled EPR spectra, as shown in FIG. 4A.

In contrast, the full-scan deconvolution algorithm of the present disclosure does not require truncation of the signal or that the EPR signal in each half cycle decay by the start of the EPR signal in the next half cycle. Provided that the responses for up-field and down-field scans are separated from m(t), the herein-disclosed full-scan algorithm outputs stable solutions with no restrictions beyond those imposed by the spin system itself. The restrictions include a requirement for linearity (see Equation 5) and the relaxation time limit expressed in Equation 8. Previously developed background removal was used for the separation of the up- and down-scan contributions.

It is important to note that a scan rate increase does not necessarily affect the signal bandwidth. RS EPR is a narrowband excitation and broadband detection method that is in comparison with the standard CW (pure narrowbanded) and pulsed (pure broadbanded) methods. The highest signal-to-noise ratio can be achieved when the signal bandwidth matches that of the detection resonator. Very small spectral broadening in the data presented in Table 1 is the result of the resonator bandwidth being slightly smaller than the signal bandwidth. No statistically significant line broadening was observed between the results obtained at 72 and 98 kHz. This is because the Larmor frequency reaches its maximum (or minimum) at the inflection points of the scan. The new full-cycle deconvolution algorithm permits a two-fold increase in the scan frequency without increasing the signal bandwidth. As a result, twice as many signal averages per unit time can be performed to additionally improve signal-to-noise. The full-cycle deconvolution algorithm of the present disclosure may be used in various EPR spectroscopy and imaging applications.

Figure 5:
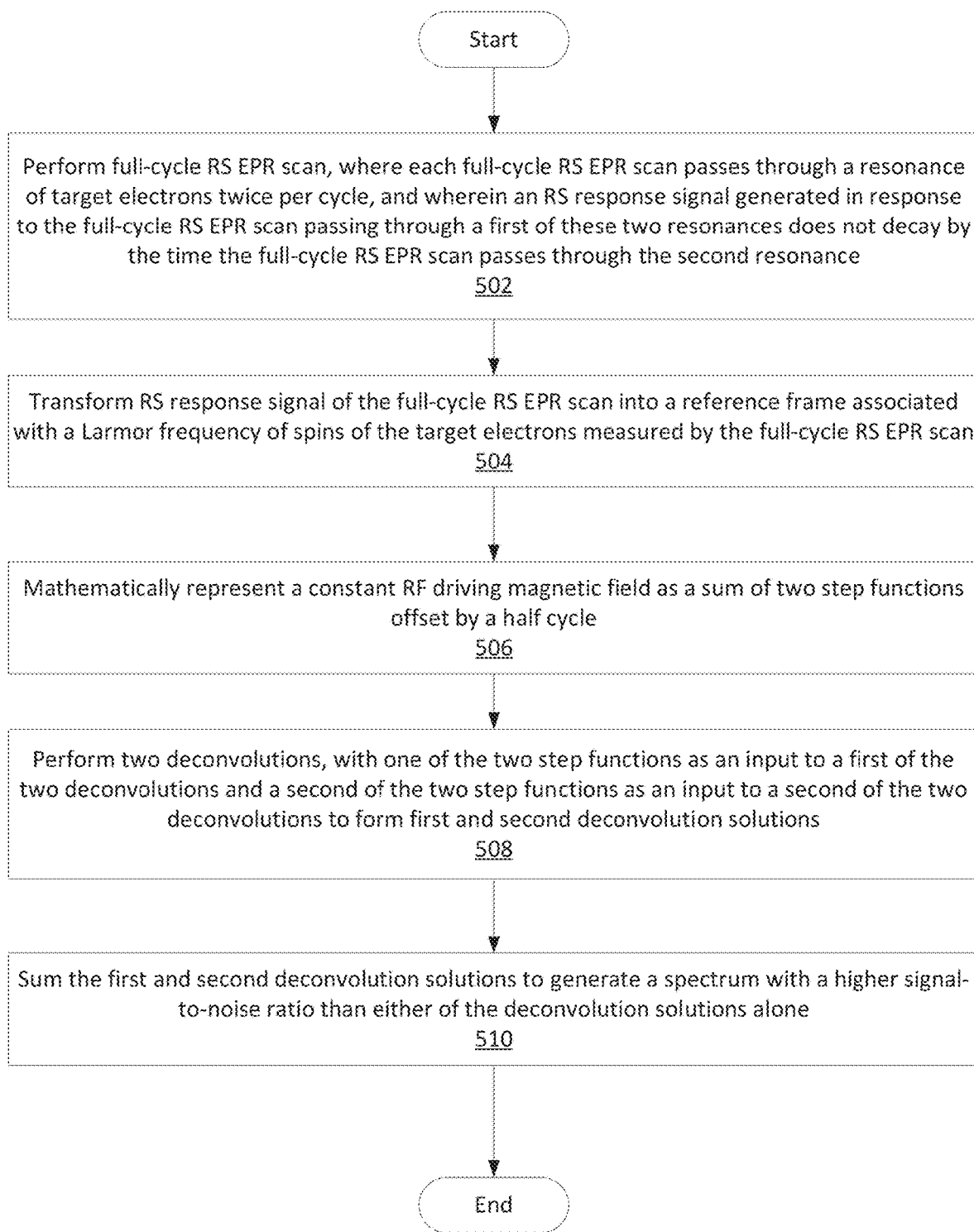
FIG. 5 shows a method of performing a full-scan rapid EPR scan.

FIG. 5 is a flowchart which may be traversed to implement a method for full-cycle rapid scan (RS) electron paramagnetic resonance (EPR). The method 500 can include performing a full-cycle RS EPR scan (Block 502). This scan can pass through a resonance of target electrons twice per cycle. Yet, unlike convention scans, the scan frequency can be high enough that an RS response signal generated in response to the full-cycle RS EPR scan passing through a first of these two resonances does not decay by the time the full-cycle RS EPR scan passes through the second resonance (see FIG. 3A). The method 500 can further include transforming the RS response signal of the full-cycle RS EPR scan into a reference frame associated with a Larmor frequency of spins of the target electrons measured by the full-cycle RS EPR scan (Block 504). The method 500 can yet further include mathematically representing a constant RF driving magnetic field of the scan as a sum of two step functions offset by a half cycle (Block 506) (see FIG. 3B). The method 500 can yet further include performing two deconvolutions (e.g., Equations 17A and 17B), with one of the two step functions (e.g., $B_1^{up}$ (t) in Equation 16) as an input to a first of the two deconvolutions and a second of the two step functions ((e.g., $B_1^{dn}$ (t) in Equation 16)) as an input to a second of the two deconvolutions, to form first and second deconvolution solutions (Block 508). The method 500 can yet further include summing the first and second deconvolution solutions to generate a spectrum with a higher signal-to-noise ratio than either of the deconvolution solutions alone (e.g., compare FIG. 4D to FIG. 4C).

Figure 6:
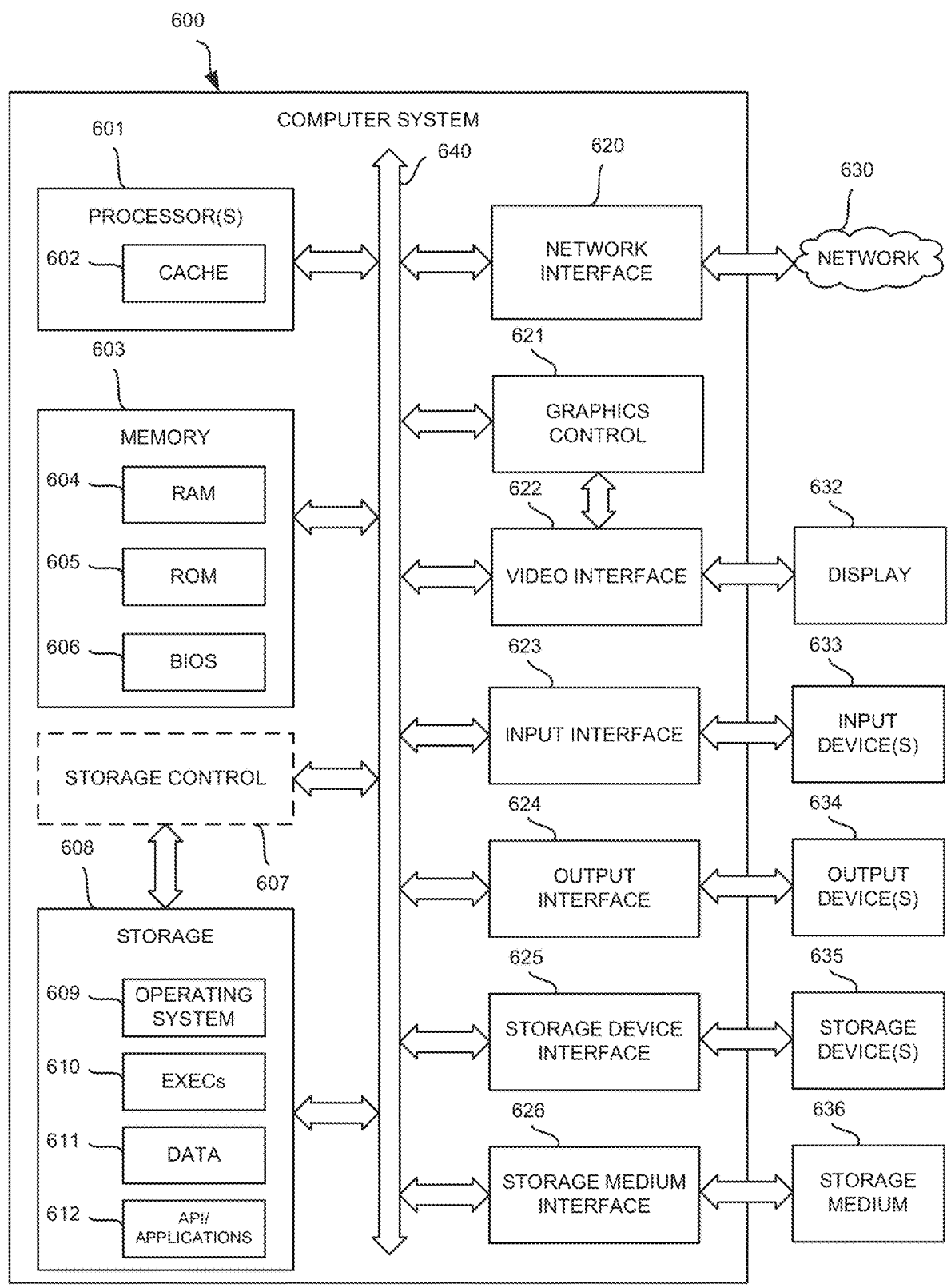
FIG. 6 shows a block diagram depicting an exemplary machine that includes a computer system within which a set of instructions can execute for causing a device to perform or execute any one or more of the aspects and/or methodologies for static code scheduling of the present disclosure.

Referring next to FIG. 6, it is a block diagram depicting an exemplary machine that includes a computer system 600 within which a set of instructions can execute for causing a device to perform or execute any one or more of the aspects and/or methodologies for static code scheduling of the present disclosure. The components in FIG. 6 are examples only and do not limit the scope of use or functionality of any hardware, software, embedded logic component, or a combination of two or more such components implementing particular embodiments.

Computer system 600 may include a processor 601, a memory 603, and a storage 608 that communicate with each other, and with other components, via a bus 640. The bus 640 may also link a display 632, one or more input devices 633 (which may, for example, include a keypad, a keyboard, a mouse, a stylus, etc.), one or more output devices 634, one or more storage devices 635, and various tangible storage media 636. All of these elements may interface directly or via one or more interfaces or adaptors to the bus 640. For instance, the various tangible storage media 636 can interface with the bus 640 via storage medium interface 626. Computer system 600 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 601 (or central processing unit(s) (CPU(s))) optionally contains a cache memory unit 602 for temporary local storage of instructions, data, or computer addresses. Processor(s) 601 are configured to assist in execution of computer readable instructions. Computer system 600 may provide functionality for the components depicted in FIG. 1 as a result of the processor(s) 601 executing non-transitory, processor-executable instructions embodied in one or more tangible computer-readable storage media, such as memory 603, storage 608, storage devices 635, and/or storage medium 636. The computer-readable media may store software that implements particular embodiments, and processor(s) 601 may execute the software. Memory 603 may read the software from one or more other computer-readable media (such as mass storage device(s) 635, 636) or from one or more other sources through a suitable interface, such as network interface 620. The software may cause processor(s) 601 to carry out one or more processes or one or more steps of one or more processes described or illustrated herein. Carrying out such processes or steps may include defining data structures stored in memory 603 and modifying the data structures as directed by the software.

The memory 603 may include various components (e.g., machine readable media) including, but not limited to, a random access memory component (e.g., RAM 604) (e.g., a static RAM "SRAM", a dynamic RAM "DRAM, etc.), a read-only component (e.g., ROM 605), and any combinations thereof. ROM 605 may act to communicate data and instructions unidirectionally to processor(s) 601, and RAM 604 may act to communicate data and instructions bidirectionally with processor(s) 601. ROM 605 and RAM 604 may include any suitable tangible computer-readable media described below. In one example, a basic input/output system 606 (BIOS), including basic routines that help to transfer information between elements within computer system 600, such as during start-up, may be stored in the memory 603.

Fixed storage 608 is connected bidirectionally to processor(s) 601, optionally through storage control unit 607. Fixed storage 608 provides additional data storage capacity and may also include any suitable tangible computer-readable media described herein. Storage 608 may be used to store operating system 609, EXECs 610 (executables), data 611, API applications 612 (application programs), and the like. Often, although not always, storage 608 is a secondary storage medium (such as a hard disk) that is slower than primary storage (e.g., memory 603). Storage 608 can also include an optical disk drive, a solid-state memory device (e.g., flash-based systems), or a combination of any of the above. Information in storage 608 may, in appropriate cases, be incorporated as virtual memory in memory 603.

In one example, storage device(s) 635 may be removably interfaced with computer system 600 (e.g., via an external port connector (not shown)) via a storage device interface 625. Particularly, storage device(s) 635 and an associated machine-readable medium may provide nonvolatile and/or volatile storage of machine-readable instructions, data structures, program modules, and/or other data for the computer system 600. In one example, software may reside, completely or partially, within a machine-readable medium on storage device(s) 635. In another example, software may reside, completely or partially, within processor(s) 601.

Bus 640 connects a wide variety of subsystems. Herein, reference to a bus may encompass one or more digital signal lines serving a common function, where appropriate. Bus 640 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 600 may also include an input device 633. In one example, a user of computer system 600 may enter commands and/or other information into computer system 600 via input device(s) 633. Examples of an input device(s) 633 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 633 may be interfaced to bus 640 via any of a variety of input interfaces 623 (e.g., input interface 623) including, but not limited to, serial, parallel, game port, USB, FIREWIRE, THUNDERBOLT, or any combination of the above.

In particular embodiments, when computer system 600 is connected to network 630, computer system 600 may communicate with other devices, specifically mobile devices and enterprise systems, connected to network 630. Communications to and from computer system 600 may be sent through network interface 620. For example, network interface 620 may receive incoming communications (such as requests or responses from other devices) in the form of one or more packets (such as Internet Protocol (IP) packets) from network 630, and computer system 600 may store the incoming communications in memory 603 for processing. Computer system 600 may similarly store outgoing communications (such as requests or responses to other devices) in the form of one or more packets in memory 603 and communicated to network 630 from network interface 620. Processor(s) 601 may access these communication packets stored in memory 603 for processing.

Examples of the network interface 620 include, but are not limited to, a network interface card, a modem, and any combination thereof. Examples of a network 630 or network segment 630 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 630, may employ a wired and/or a wireless mode of communication. In general, any network topology may be used.

Information and data can be displayed through a display 632. Examples of a display 632 include, but are not limited to, a liquid crystal display (LCD), an organic liquid crystal display (OLED), a cathode ray tube (CRT), a plasma display, and any combinations thereof. The display 632 can interface to the processor(s) 601, memory 603, and fixed storage 608, as well as other devices, such as input device(s) 633, via the bus 640. The display 632 is linked to the bus 640 via a video interface 622, and transport of data between the display 632 and the bus 640 can be controlled via the graphics control 621.

In addition to a display 632, computer system 600 may include one or more other peripheral output devices 634 including, but not limited to, an audio speaker, a printer, and any combinations thereof. Such peripheral output devices may be connected to the bus 640 via an output interface 624. Examples of an output interface 624 include, but are not limited to, a serial port, a parallel connection, a USB port, a FIREWIRE port, a THUNDERBOLT port, and any combinations thereof.

In addition, or as an alternative, computer system 600 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for full-cycle rapid scan (RS) electron paramagnetic resonance (EPR), the method comprising:
    performing a full-cycle RS EPR scan, where each full-cycle RS EPR scan passes through a resonance of target electrons twice per cycle, and wherein an RS response signal generated in response to the full-cycle RS EPR scan passing through a first of these two resonances does not decay by the time the full-cycle RS EPR scan passes through the second resonance;
    transforming the RS response signal of the full-cycle RS EPR scan into a reference frame associated with a Larmor frequency of spins of the target electrons measured by the full-cycle RS EPR scan;
    mathematically representing a constant RF driving magnetic field as a sum of two step functions offset by a half cycle;
    performing two deconvolutions, with one of the two step functions as an input to a first of the two deconvolutions and a second of the two step functions as an input to a second of the two deconvolutions, to form first and second deconvolution solutions; and
    summing the first and second deconvolution solutions to generate a spectrum with a higher signal-to-noise ratio than either of the deconvolution solutions alone.

2. The method of claim 1, wherein the first of the two step functions corresponds to an up half of the full-cycle RS EPR scan and the second of the two step functions corresponds to a down half of the full-cycle RS EPR scan.

3. The method of claim 2, wherein the full-cycle RS EPR scan involves a first constant magnetic field; a second constant frequency RF magnetic field; and a third magnetic field scanning sinusoidally in magnetic field strength with a frequency of the scanning being lower than the frequency of the RF magnetic field.

4. The method of claim 1, wherein the deconvolving is done in the magnetic field domain.

5. The method of claim 2, wherein a sampling interval is less than $2\Delta B$, wherein:

$$\Delta B = 2\pi f_s/\gamma.$$

6. The method of claim 2, wherein the two deconvolutions are performed on the following equations:

$$S^{up}(-B) \propto FT[\mu^{up}(t)]/FT[d(t)B_1^{up}(t)], 0 \leq t < P$$

$$S^{dn}(-B) \propto FT[\mu^{dn}(t)]/FT[d(t)B_1^{dn}(t)], 0 \leq t < P;$$

wherein:
$S^{up}$ is a half-scan up cycle, $S^{dn}$ is a half-scan down cycle;
$B_1^{up}(t)$ is a first step function input to a first of the two deconvolutions and $B_1^{dn}(t)$ is a second step functions input to the second of the two deconvolutions;
FT is a Fourier Transformation; and
$0 < t < P$ is a full scan period.

7. A system for full-cycle rapid scan (RS) electron paramagnetic resonance (EPR), the system comprising:
a processing portion with one or more processing components therein;
a memory coupled to the processing portion;
a full-cycle RS EPR scanning module stored on the memory and executable on the processing portion to:
perform a full-cycle RS EPR scan, where each full-cycle RS EPR scan passes through a resonance of target electrons twice per cycle, and wherein an RS response signal generated in response to the full-cycle RS EPR scan passing through a first of these two resonances does not decay by the time the full-cycle RS EPR scan passes through the second resonance;
transform RS response signal of the full-cycle RS EPR scan into a reference frame associated with a Larmor frequency of spins of the target electrons measured by the full-cycle RS EPR scan;
mathematically represent a constant RF driving magnetic field as a sum of two step functions offset by a half cycle;
perform two deconvolutions, with one of the two step functions as an input to a first of the two deconvolutions and a second of the two step functions as an input to a second of the two deconvolutions, to form first and second deconvolution solutions; and
sum the first and second deconvolution solutions to generate a spectrum with a higher signal-to-noise ratio than either of the deconvolution solutions alone.

8. The system of claim 7, wherein the first of the two step functions corresponds to an up half of the full-cycle RS EPR scan and the second of the two step functions corresponds to a down half of the full-cycle RS EPR scan.

9. The system of claim 8, wherein the full-cycle RS EPR scan involves a first constant magnetic field; a second constant frequency RF magnetic field; and a third magnetic field scanning sinusoidally in magnetic field strength with a frequency of the scanning being lower than the frequency of the RF magnetic field.

10. The system of claim 7, wherein the deconvolving is done in the magnetic field domain.

11. The system of claim 8, wherein a sampling interval is less than $2\Delta B$, wherein: $\Delta B = 2\pi f_s/\gamma.$ 12. The system of claim 8, wherein the two deconvolutions are performed on the following equations:

$$S^{up}(-B) \propto FT[\mu^{up}(t)]/FT[d(t)B_1^{up}(t)], 0 \leq t < P$$

$$S^{dn}(-B) \propto FT[\mu^{dn}(t)]/FT[d(t)B_1^{dn}(t)], 0 \leq t < P;$$

wherein:
$S^{up}$ is a half-scan up cycle, $S^{dn}$ is a half-scan down cycle;
$B_1^{up}(t)$ is a first step function input to a first of the two deconvolutions and $B_1^{dn}(t)$ is a second step functions input to the second of the two deconvolutions;
FT is a Fourier Transformation; and
$0 < t < P$ is a full scan period.

13. A non-transitory, tangible computer readable storage medium, encoded with processor readable instructions to perform a method for full-cycle rapid scan (RS) electron paramagnetic resonance (EPR), the method comprising:
performing a full-cycle RS EPR scan, where each full-cycle RS EPR scan passes through a resonance of target electrons twice per cycle, and wherein an RS response signal generated in response to the full-cycle RS EPR scan passing through a first of these two resonances does not decay by the time the full-cycle RS EPR scan passes through the second resonance;
transforming RS response signal of the full-cycle RS EPR scan into a reference frame associated with a Larmor frequency of spins of the target electrons measured by the full-cycle RS EPR scan;
mathematically representing a constant RF driving magnetic field as a sum of two step functions offset by a half cycle;
performing two deconvolutions, with one of the two step functions as an input to a first of the two deconvolutions and a second of the two step functions as an input to a second of the two deconvolutions, to form first and second deconvolution solutions; and
summing the first and second deconvolution solutions to generate a spectrum with a higher signal-to-noise ratio than either of the deconvolution solutions alone.

14. The non-transitory, tangible computer readable storage medium of claim 13, wherein the first of the two step functions corresponds to an up half of the full-cycle RS EPR scan and the second of the two step functions corresponds to a down half of the full-cycle RS EPR scan.

15. The non-transitory, tangible computer readable storage medium of claim 14, wherein the full-cycle RS EPR scan involves a first constant magnetic field; a second constant frequency RF magnetic field; and a third magnetic field scanning sinusoidally in magnetic field strength with a frequency of the scanning being lower than the frequency of the RF magnetic field.

16. The non-transitory, tangible computer readable storage medium of claim 13, wherein the deconvolving is done in the magnetic field domain.

17. The non-transitory, tangible computer readable storage medium of claim 14, wherein a sampling interval is less than $2\Delta B$, wherein: $\Delta B = 2\pi f_s/\gamma.$ 18. The non-transitory, tangible computer readable storage medium of claim 14, wherein the two deconvolutions are performed on the following equations:

$$S^{up}(-B) \propto FT[\mu^{up}(t)]/FT[d(t)B_1^{up}(t)], 0 \leq t < P$$

$$S^{dn}(-B) \propto FT[\mu^{dn}(t)]/FT[d(t)B_1^{dn}(t)], 0 \leq t < P;$$

wherein:

$S^{up}$ is a half-scan up cycle, $S^{dn}$ is a half-scan down cycle;

$B_1^{up}(t)$ is a first step function input to a first of the two deconvolutions and $B_1^{dn}(t)$ is a second step functions input to the second of the two deconvolutions;

FT is a Fourier Transformation; and $0<t<P$ is a full scan period.

* * * * *